(12) United States Patent
Decreton et al.

(10) Patent No.: US 10,310,269 B2
(45) Date of Patent: Jun. 4, 2019

(54) METHOD FOR VIRTUAL TESTING OF AT LEAST ONE LENS HAVING A PREDETERMINED OPTICAL FEATURE AND ASSOCIATED DEVICE

(71) Applicant: ESSILOR INTERNATIONAL (Compagnie Generale d'Optique), Charenton-le-Pont (FR)

(72) Inventors: Bruno Decreton, Charenton-le-Pont (FR); Florence Bazaille, Charenton-le-Pont (FR); Dinesh Ahangama, Charenton-le-Pont (FR); Claire Le Covec Mazzella, Charenton-le-Pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 0 days.

(21) Appl. No.: 15/661,524

(22) Filed: Jul. 27, 2017

(65) Prior Publication Data
US 2018/0031844 A1   Feb. 1, 2018

(30) Foreign Application Priority Data
Jul. 29, 2016  (EP) .................................. 16305991

(51) Int. Cl.
*A61B 3/00* (2006.01)
*G02C 7/02* (2006.01)
(Continued)

(52) U.S. Cl.
CPC .......... *G02B 27/0172* (2013.01); *A61B 3/005* (2013.01); *G01M 11/02* (2013.01);
(Continued)

(58) Field of Classification Search
None
See application file for complete search history.

(56) References Cited

U.S. PATENT DOCUMENTS

| 9,404,863 B2 | 8/2016 | Citek et al. |
| 9,574,875 B2 | 2/2017 | Dubois |

(Continued)

FOREIGN PATENT DOCUMENTS

| CN | 103217273 | 7/2013 |
| CN | 103998911 | 8/2014 |

(Continued)

OTHER PUBLICATIONS

EP Search Report, dated Jan. 2, 2017, from corresponding EP application No. 16 30 5991.

(Continued)

*Primary Examiner* — Motilewa Good Johnson
(74) *Attorney, Agent, or Firm* — Young & Thompson

(57) ABSTRACT

The disclosed method uses a headset to be placed on the head of an individual, an image capture apparatus, and a sensor adapted to measure a value of a first parameter linked to the luminous intensity of a light present in the environment of the individual with a wavelength included in a predetermined wavelength range. The method includes the following steps: a) capturing at least an image of the environment with the image capture apparatus; b) measuring the measured value of the first parameter; c) displaying on a screen of the headset a corrected image based on the captured image, taking into account the measured value and the optical feature of the lens. An associated electronic device is also described.

13 Claims, 2 Drawing Sheets

(51) Int. Cl.
    *G01M 11/02* (2006.01)
    *G02B 27/01* (2006.01)
(52) U.S. Cl.
    CPC ........ *G02C 7/028* (2013.01); *G02B 2027/014* (2013.01); *G02B 2027/0118* (2013.01); *G02B 2027/0138* (2013.01); *G02B 2027/0178* (2013.01)

(56) References Cited

U.S. PATENT DOCUMENTS

| | | | |
|---|---|---|---|
| 2005/0168569 A1 | 8/2005 | Igarashi et al. | |
| 2013/0335543 A1 | 12/2013 | Hilkes et al. | |
| 2014/0218281 A1 | 8/2014 | Amayeh et al. | |
| 2016/0301844 A1* | 10/2016 | Smith | G01N 21/00 |
| 2017/0161951 A1* | 6/2017 | Fix | G09G 5/00 |

FOREIGN PATENT DOCUMENTS

| | | |
|---|---|---|
| CN | 104011532 | 8/2014 |
| CN | 104903818 | 9/2015 |
| CN | 105181299 | 12/2015 |
| EP | 2 856 931 A1 | 4/2015 |
| EP | 2 940 556 A1 | 11/2015 |
| EP | 2 958 035 A1 | 12/2015 |
| JP | H07-288754 A | 10/1995 |

OTHER PUBLICATIONS

Chinese Office Action for Application No. 201710626645, dated Jan. 28, 2019, with English translation provided.

* cited by examiner

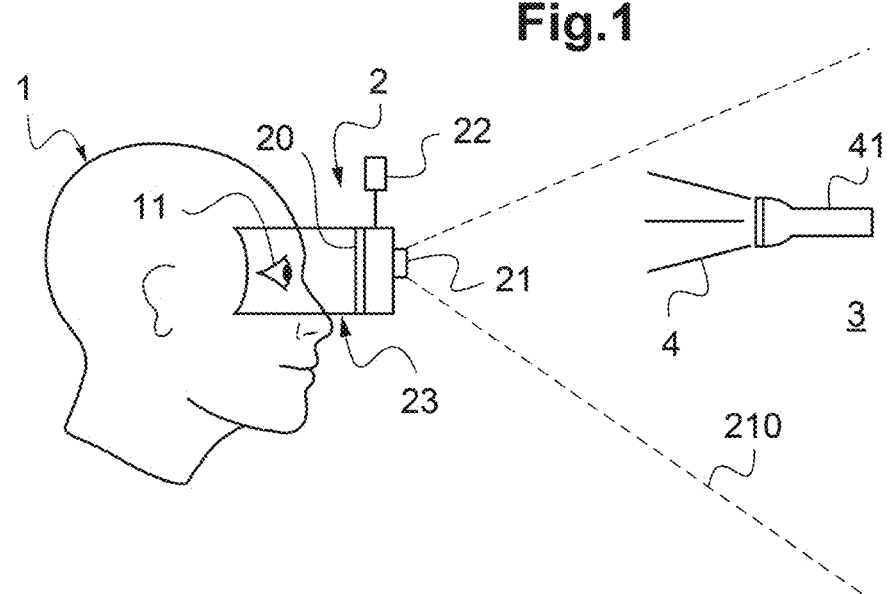
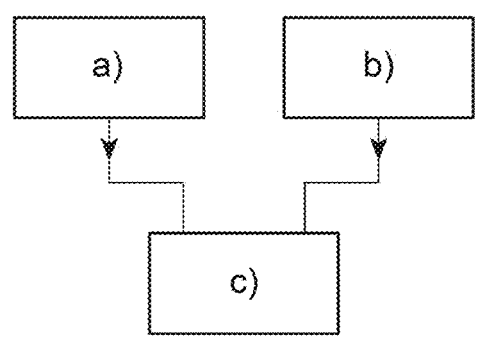

METHOD FOR VIRTUAL TESTING OF AT LEAST ONE LENS HAVING A PREDETERMINED OPTICAL FEATURE AND ASSOCIATED DEVICE

TECHNICAL FIELD OF THE INVENTION

The invention relates to a method for virtually testing at least one lens having a predetermined feature and adapted to be used in eyeglasses by an individual.

The invention relates also to an electronic device implementing such a virtual testing method.

BACKGROUND INFORMATION AND PRIOR ART

Light having a wavelength in a particular visible blue range or ultraviolet range is potentially harmful to an individual's eye, though barely, or not, visible to him/her.

Hence, most individuals evaluate poorly their eye protective needs against such blue and/or ultraviolet radiations.

In particular, when selecting a lens to be used in eyeglasses, by testing several kinds of lenses, a non-specialist individual barely takes into account optical protection features of these lenses e.g. lens features related to optical transmission and/or reflection of blue/ultraviolet light, all the more these features are not, or only faintly perceptible directly.

SUMMARY OF THE INVENTION

Therefore one object of the invention is to provide a method enabling an individual to perceive the highly frequent presence in his/her environment of a blue/ultraviolet light and/or said light harmfulness to his/her eyes, and to test the effect of a lens in terms of transmission and/or reflection of said light.

The above object is achieved according to the invention by providing a method for virtually testing at least one lens having a predetermined feature and adapted to be used in eyeglasses by an individual, said method using:
- a headset, comprising at least a screen, the headset being adapted to be placed on the head of an individual such that said screen is disposed in front of at least one eye of the individual,
- an image capture apparatus adapted to capture an image of the environment of the individual, and
- a sensor adapted to measure a value of a first parameter comprising a luminous intensity, and/or a luminance, and/or an illumination specific to a light present in said environment of the individual with a wavelength comprised in a predetermined wavelength range, wherein the following steps are performed:

a) capturing at least an image of said environment of the individual with said image capture apparatus, b) measuring said measured value of said first parameter corresponding to said image captured in step a), c) displaying on said screen of the headset a corrected imagebased on said captured image, taking into account said measured value of the first parameter and said optical feature of the lens.

Said method enables the individual to visualize, by means of said corrected image, the presence in the environment of said light having said wavelength comprised in said predetermined range, for instance a blue/ultraviolet light, even if said light would be invisible or only faintly visible, directly to the naked eyes of the individual.

In addition, by taking into account said optical feature of said tested lens, the method enables the individual to perceive said lens effect, both on visible and, potentially non visible radiations.

As the corrected image that is displayed is based on said captured image, it shows to the individual a so-called <<augmented reality>> view of said environment, that is to say, a view of said environment showing simultaneously elements of said environment actually visible with a naked eye, and other elements, invisible or faintly visible to the naked eye.

This augmented reality view is particularly beneficial in order to test an ophthalmic lens in real life conditions. More precisely, it is especially adapted to test non-visually perceptible optical features of this lens.

The method according to the invention indeed allows to alert the individual on the presence of potentially harmful light in his/her environment and to display for this individual the protective effect of the tested lens on this light.

According to one particular aspect of the invention, when said measured value fulfils a predetermined criterion, a graphical representation of said light having said wavelength comprised in said predetermined wavelength range is superimposed to the captured image, said graphical representation comprising elements representing light rays and/or photons.

According to one particular aspect of the invention, in step c), the corrected image comprises a graphical representation of said light having said wavelength comprised in said predetermined wavelength range, said graphical representation comprising elements representing light rays and/or photons, this graphical representation having features that depend on said optical feature of the lens.

According to one particular aspect of the invention, said graphical representation comprises features that depend on said measured value of the first parameter.

According to one particular aspect of the invention, said features of the graphical representation comprise geometrical and/or display features.

According to one particular aspect of the invention, in step a), a plurality of images is captured, and in step c), a plurality of corrected images is determined.

According to one particular aspect of the invention, in step c), the plurality of corrected images comprises an animated graphical representation of said light having said wavelength comprised in said predetermined wavelength range, said animated graphical representation comprising elements representing light rays and/or photons, a frequency of appearance of said elements in said plurality of corrected images depending on said measured value of the first parameter and on said optical feature of the lens.

According to one particular aspect of the invention, in step b), said measured value is determined by a direct measurement of said first parameter in said environment.

According to one particular aspect of the invention, in step b), said measured value is determined by an indirect measurement of said first parameter on said image captured in step a).

According to one particular aspect of the invention, said predetermined wavelength range comprises wavelengths in the visible blue range, between 400 and 460 nanometers and/or in the Ultra-Violet range, between 280 and 400 nanometers.

According to another particular aspect of the invention, the method comprises a step of determining a position of a source of said light having said wavelength comprised in said predetermined wavelength range, in said captured image and wherein, in step c), said position being taken into account to determine said corrected image.

According to one particular aspect of the invention, in step c), said optical feature of the lens that is taken into account is at least one of:
- a reflection coefficient of an object-side face of the lens within the predetermined wavelength range;
- a transmission coefficient of the lens within the predetermined wavelength range; and
- a reflection coefficient of an eye-side face of the lens within the predetermined wavelength range.

The above mentioned object is also achieved according to the invention by providing an electronic device for virtual testing of at least one lens having a predetermined optical feature and adapted to be used in eyeglasses by an individual, the electronic device comprising:
- a headset, comprising at least a screen, adapted to be placed on the head of an individual such that said screen is disposed in front of one eye of the individual,
- an image capture apparatus adapted to capture an image of the environment of the individual, and
- a sensor adapted to measure a value of a first parameter comprising a luminous intensity, and/or a luminance, and/or an illumination specific to a light present in said environment of the individual with a wavelength comprised in a predetermined wavelength range, said device being programmed to execute the following steps:
a) capturing at least an image of said environment of the individual with said image capture apparatus,
b) measuring said measured value of said first parameter corresponding to said image captured in step a),
c) displaying on said screen of the headset a corrected image based on said captured image modified to take into account said measured value of the first parameter and said optical feature of the lens.

The optional features defined above in terms of method can also be applied to said electronic device.

DETAILED DESCRIPTION OF EXAMPLES

The description which follows with reference to the appended drawings, which are given by way of non-limiting examples, will make it easy to understand the essence of the invention and how it can be achieved.

In the appended drawings:

FIG. 1 is a schematic representation of an electronic device for virtual testing of at least one lens adapted to be used in eyeglasses by an individual, according to the invention;

FIG. 2 is a schematic representation of the mains steps of a method, according to the invention, for virtual testing at least one lens, that can be performed using the electronic device of FIG. 1;

FIG. 1 shows an electronic device 2 for implementing the method according to the invention.

Figure 3:
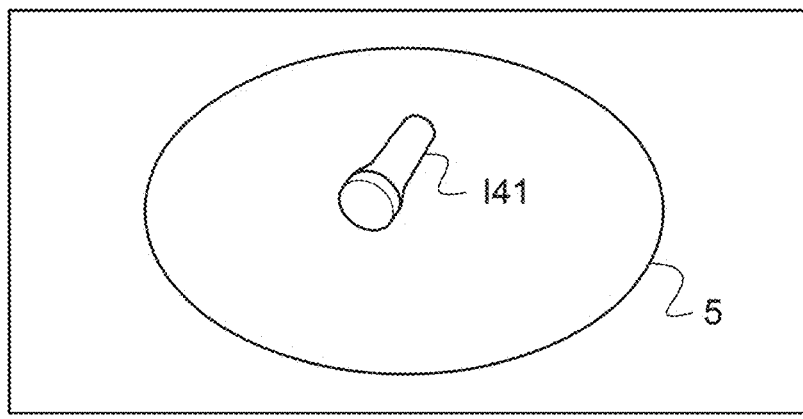
FIGS. 3 to 5 are schematic examples of corrected images determined in step c) of FIG. 2.

This electronic device 2 is designed for virtual testing of at least one lens, that has a predetermined optical feature, and is adapted to be mounted in an eyeglasses frame.

This lens, which is an ophthalmic lens, is made of a bulk material, such as a plastic material, shaped to present two opposite faces. The face of the lens that is on the side of a user's eye, when the lens is used in eyeglasses worn by this user, is called the "eye-side" face, while the other of these two faces is called the "object-side" face of the lens.

Each of the object-side face and the eye-side face of the lens has a light reflection coefficient for light depending on light wavelength. The reflection coefficient of each of these faces may depend in particular on a stack of optical coatings deposited on this face.

Transmission of light through the bulk material of the lens, between the object-side face and the eye-side face of the lens, which also depends on light wavelength, is characterized by a transmission coefficient, which is related to the bulk material light absorption within said wavelength range.

The overall transmission of the lens, defined as a ratio between a luminous intensity of a radiation after going through the lens, and a luminous intensity of that radiation before going through the lens, depends on the reflection coefficient on the object-side face, on the above-mentioned transmission coefficient, and on the reflection coefficient on the eye-side face.

Consequently, a predetermined optical feature of the tested lens may in particular comprise one of:
- the reflection coefficient of the object-side face of the lens within a predetermined wavelength range,
- the transmission coefficient through the lens material, within the predetermined wavelength range, and
- the reflection coefficient of the eye-side face of the lens within the predetermined wavelength range.

Said optical feature has thus, here, a direct influence on the overall transmission of the lens within said predetermined wavelength range.

The electronic device 2 is a so-called augmented reality device, comprising a headset 23, adapted to be placed on a head 1 of the individual, at the eyes level.

The headset 23 comprises a least a screen 20, such as a Liquid Crystal Display screen, or an Oled display screen and is configured so that said screen 20 is disposed in front of at least one eye 11, of the individual, when the headset 23 is placed on the head 1 of the user in its position of use, as represented schematically on FIG. 1. The screen is preferably positioned in front of the two eyes of the individual.

The electronic device 2 comprises also an image capture apparatus, such as a camera 21, adapted to capture an image of an environment 3 of the individual.

Here, the camera 21 is oriented opposite the headset 23 screen 20. So, when the headset 23 is placed on the individual's head 1, the field of view 210 of the camera encompasses a part of the individual's environment 3 that is locate in front of the individual's head 1.

The camera 21 is mounted on or integrated to the headset 23.

In the present example, the camera 21 and the screen 20 may be two parts included in a mobile-phone, or so-called smartphone, mounted on a frame of the headset.

The electronic device 2 comprises also a sensor 22, adapted to measure a value of a first parameter linked to the luminous intensity of a light 4 present in said environment 3 of the individual with a wavelength comprised in said predetermined wavelength range.

This first parameter comprises here a luminous intensity, and/or a luminance, and/or an illumination specific to the light 4 present in the environment 3 of the individual, having said wavelength comprised in said predetermined range.

In this case, the sensor 22 can thus be achieved by means of:
- a photodiode or a phototransistor, having a non-zero sensitivity within said predetermined wavelength range, and an bandpass optical filter, having a transmission higher within said predetermined wavelength range than outside of it.

In other, non-represented embodiments of the electronic device, the sensor may comprise means for processing an image captured by said image capture apparatus.

In such a case, the measured value is measured by an indirect measurement comprising an image capture by the camera and a subsequent processing of this image for searching a light source search within this image.

The light source is identified within the captured image, its position in the image and/or in space may be determined, and the measured value of the first parameter is determined based on these information.

Said predetermined wavelength range, selectively transmitted by said filter, comprises here preferably wavelengths in the visible blue range, between 400 and 460 nanometers and/or in the Ultra-Violet range, between 280 and 400 nanometers.

As a variant, said predetermined wavelength range may comprise wavelengths from any other wavelengths range, preferably wavelength ranges which are potentially harmful to a human eye.

The sensor 22 is mounted on the headset 23, as represented on FIG. 1, and is oriented in the same manner as the camera 21, that is to say oriented toward the environment in front of the individual, opposite from the screen.

So, when the headset 23 is placed on the head 1 of the individual, in its position of use, the sensor 22 is oriented toward the part of the environment 3 located in front of the head 1 of the individual. The above mentioned light 4, to which the sensor 22 is sensitive to, then comes from the part of the environment 3 located in front of the head 1 of the individual.

According to an optional feature of the device, the sensor 22 may be swiveled between a first position, in which the sensor is oriented in the same manner as the camera opposite to the screen, and a second position, in which the sensor is oriented opposite to the camera, in the same manner as the headset screen 20.

When the sensor is oriented similarly in the same manner as the screen and the headset is placed on the head of the individual, the sensor is then sensitive to light coming from the back of the individual's head 1.

In a variant, the device may comprise another sensor, the two sensors having opposite orientations. In another variant, the sensor may be held by a support separated from the headset. In a general manner, the device may comprise a plurality of sensors oriented in different directions.

The above-mentioned light 4, that comprises here a least a wavelength in the visible blue range or in the Ultra-Violet range, may, as it is the case in the situation represented on FIG. 1, be generated by a torch 41. It may also be emitted by a blue-light/UV light stationary lamp, by a screen of a computer, touch-screen tablet or mobile phone, or by the Sun.

The electronic device 2 comprises also an electronic control unit (not represented on the figures), connected to the camera 21, the sensor 22 and the screen 20. This electronic control unit is adapted to receive data representatives of images captured by the camera and data representative of the measured value of the first parameter. This electronic control unit comprises here one or more processing units and memories of the smartphone mounted on the frame of the headset.

The electronic control unit of the electronic device 2 is programmed to execute the following steps (schematically represented on FIG. 2) of the method of the invention:

a) capturing at least an image of said environment 3 of the individual with said image capture apparatus, here the camera 21, b) measuring said measured value of said first parameter corresponding to said image captured in step a), c) displaying on said screen 20 of the headset 23 a corrected image based on said captured image modified to take into account said measured value of the first parameter and said optical feature of the lens.

The device 2 enables the individual wearing the headset 23 to perceive in a realistic manner, via said corrected image, the presence of said light 4, harmful to his/her eyes 11, in his/her environment 3, and to test the effect of said lens in terms of transmission and/or reflection of said light.

The device 2 thus enables the individual to test the protective effect of said lens regarding said harmful light in a realistic manner, even though said light 4 is not visible or only faintly visible to his/her naked eyes.

So, the device 2 helps greatly the individual when comparing different lenses in order to select one to be used in his eyeglasses.

In step a), the device 2 is programmed in order to capture at least one image of the scene opposite to the screen of the device 2.

According to an optional feature, the device 2 is programmed so that a plurality of images is captured in step a). This plurality of images is captured by the device's camera 21, successively in time. It may form a movie of the scene in front of the individual.

In the example shown on the appended figure, the sensor 22 is separated from the camera 21. The device is then programmed to measure the measured value of the first parameter directly, by this sensor 22 in step b).

In the variant in which the sensor is achieved by means of the image sensor of the camera, the measured value of the first parameter is measured, in step b), by processing an image captured by the camera, for instance the image, or the plurality of images, captured in step a).

The device 2 is programmed to ensure that the measured value of the first parameter is measured while said image, or while said plurality of images, are captured in step a), or at least it is measured to correspond to the value of the first parameter while the image or the plurality of images are captured.

In other words:

the measure of said measured value and the capture of said image, or the capture of one of the images of said plurality of images, are preferably simultaneous, or at least separated in time by a duration shorter than a given limit, for instance shorter than 1 second; preferably shorter than 20 milliseconds.

According the method of the invention, in step c), the corrected image displayed is based on the image captured in step a).

It comprises first a feature, superimposed to the image captured in step a), showing the outline of the tested lens, virtually placed in front of the individual's eye, as a foreground to the environment, the environment being shown in the background.

Figure 4:
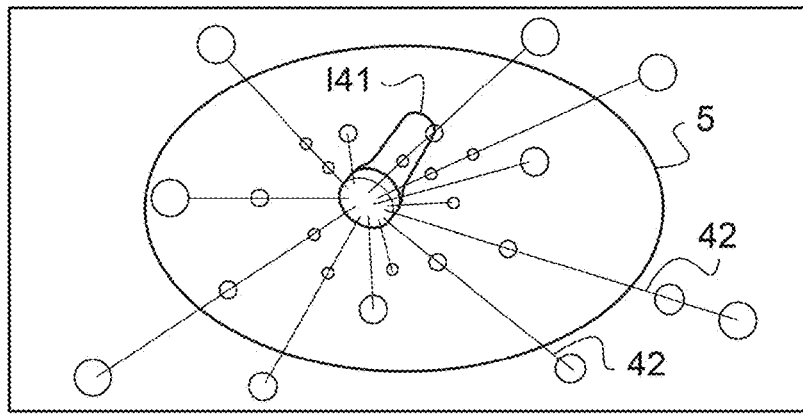
Figure 5:
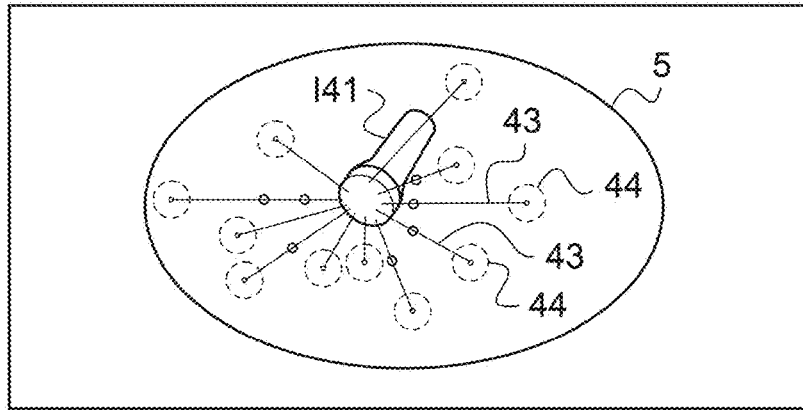

This feature may show schematically, for instance, the edge 5 of the lens's faces, as represented on FIGS. 3 to 5, or an eyeglasses frame in which the lens could be mounted.

The part of the image included in the outline may be modified in order to take into account the refraction of the lens. Alternatively, the part of the image outside the outline may be blurred to show the background.

In a first embodiment of the device and method according to the invention, the device 2 is programmed to superimpose, to the image captured in step a), a graphical representation of the light 4, detected via the measure of said measured value, when said measured value fulfils a predetermined criterion.

Here, this predetermined criterion corresponds to being over a given threshold value. So, the device 2 is programmed here to perform the following steps of the method according to the invention:
  to compare the measured value to a threshold value, and
  to superimpose the representation of said light 4 to the image captured in step b), when said measured value is over over said threshold value.

In this first embodiment, the measured value of the first parameter is thus taken into account, in the determination of the corrected image, in an all-or-nothing manner, considering only the fact the measured value is over, or below, said threshold value.

This threshold value may for instance be equal to a value of the first parameter in an environment comprising no specific source of visible blue light or Ultra-Violet light, that is to say in an environment without UV-lamps, blue/UV leds, or direct sunlight.

According to the invention, the device 2 is programmed also such that the graphical representation of said light 4 depends on the optical feature of the lens.

More precisely, here, when the optical feature of the lens is such that its overall transmission within said wavelength range is over a first transmission threshold, then, the graphical representation of said light is such that it evidences transmission of this light 4 through the lens.

And when the optical feature of the lens is such that its overall transmission within said wavelength range is below a second transmission threshold, then, the graphical representation of said light is such that it evidences a stop of this light 4 by the lens.

So, when the optical feature is representative of a high reflection coefficient of the eye-side face and/or object-side face of the lens within the predetermined wavelength range, for example, the graphical representation of said light is such that it evidences a stop of this light 4 by the lens.

The first transmission threshold is comprised, for example, in a range between 80% and 100%, while the second transmission threshold is comprised, for example, in a range between 1% and 80%.

So, in this first embodiment, the device is programmed to determine the corrected image to be displayed according to three different cases:
  i) when the measured value of the first parameter is below the threshold value, no graphical representation of said light 4 is added to the captured image,
  ii) when the measured value of the first parameter is over the threshold value, and the predetermined optical feature of the lens is such that its overall transmission is over the first transmission threshold, then, the graphical representation of said light 4 is superimposed to the captured image, showing the transmission of this light 4 through the lens, and
  iii) when the measured value of the first parameter is over the threshold value, and the predetermined optical feature of the lens is such that its overall transmission is below the second transmission threshold, then, the graphical representation of said light 4 is superimposed to the captured image, showing this light 4 stopped by the lens.

Three examples IMGi), IMGii) and IMGiii), of the corrected image are represented schematically, respectively for the i), ii), and iii) cases, on FIGS. 3, 4 and 5.

The captured image, on which these corrected images IMGi), IMGii) and IMGiii) are based, is captured in the situation represented schematically on FIG. 1. This captured image thus includes an image I41 of the torch 41 represented on FIG. 1.

Each of these corrected images IMGi), IMGii) and IMGiii) includes also the above-mentioned feature showing the edge 5 of the lens's faces.

Corrected image IMGii) shows said light 4 transmission through the lens by means of a graphical representation of light rays 42 traversing the lens.

Corrected image IMGiii) shows said light 4 stopped by the lens by means of a graphical representation of light rays 43 stopped by the lens, an impact 44 on the lens evidencing this stop.

As illustrated by this first exemplary embodiment, thanks to the invention, the individual can quickly test the protective effect of the lens against harmful, non necessarily visible, light. The invention enables a realistic, though augmented, representation of the individual's environment 3, making this test particularly striking.

In a variant of this first embodiment, the electronic device may be programmed:
  to compare the overall transmission of the lens to more than two transmission thresholds, and
  to determine the graphical representation of said light depending on these comparisons' results,
in order to take into account the optical feature of the lens more acutely.

In another variant of this first embodiment, the electronic device may be programmed to determine the graphical representation of said light, in a manner depending continuously on a value representative of the optical feature of the lens.

For example, this graphical representation may show optical rays traversing the lens, and optical rays stopped by the lens, the traversing optical rays being all the more numerous, compared to the stopped optical rays, as the overall transmission of the lens within said predetermined wavelength range is high.

In yet another variant, the graphical representation of said light having said predetermined wavelength may be such that it evidences that the reflection of this light in direction of the eyes of the individual is reduced when the lens exhibits an appropriate eye-side reflection coefficient.

In the second embodiment of the electronic device 2 and the method according to the invention, this device is programmed to determine the corrected image so that it contains a graphical representation of the light 4 having said predetermined wavelength range, this graphical representation having features that depend on the measured value of the first parameter.

The device 2 is programmed more finely, in this second embodiment, so that geometrical and/or display features of the graphical representation of said light 4 depend on the measured value of the first parameter.

Said graphical representation may comprise elements such as:
  elements representing light rays, such as straight lines, arising from the source 41 of said light 4, and/or
  elements representing photons, such as balls, stars, or concentric circles.

In such a case, the geometrical features of the graphical representation of said light comprise in particular the number and/or size and/or brightness and/or color and/or shape of these elements.

The device 2 may thus be programmed, for instance, so that, in this graphical representation, lines representing light rays, or balls representing photons, are all the more numerous as the measured value of said first parameter is high.

The device 2 is also programmed, in this second embodiment, so that these features depend on said optical feature of the lens. For example, impacts representing photons stopped by the lens may be all the more numerous as the measured value is high, and that the overall transmission of the lens is low.

In a variant of this second embodiment, the graphical representation of said light, whose features depends on the luminous intensity of the light represented via said measured value, may be superimposed to the captured image only when the measured value is higher than threshold value, as it is the case in the first embodiment.

In any of the first and second embodiments of the invention, the device 2 may be programmed in order to determine a couple of corrected images and to display one of these corrected images in a part of the screen 20 facing the left eye of the individual, and the other of these corrected images in a part of the screen 20 facing the right eye of the individual, to provide a stereoscopic, 3-D like view of the environment 3 and/or elements representing said light 4 to the individual.

As mentioned above, the device 2 may be programmed in order to capture a plurality of images, in step a).

In such a case, the device 2 is preferably programmed in order to determine, in step c), a plurality of corrected images. In other words, in that case, the device 2 is programmed to capture a film of the environment in step a), and to determine a corrected film in step c).

To this end, the device 2 is programmed for example so that the plurality of corrected images comprises a animated graphical representation of said light 4, such as small balls or stars coming towards the individual eye. According to an optional feature, the device 2 may then be programmed, so that this animated graphical representation comprises elements, such as those mentioned above, whose frequency of appearance and/or displacement speed depends on the measured value of the first parameter and on the optical feature of the lens. For example, this frequency of appearance and/or displacement speed increases, and is all the higher that the measured value of the first parameter is high, and that the overall transmission of the lens is high.

According to an optional feature of the electronic device 2, the predetermined optical feature, taken into account at step c), may further comprise a transmission coefficient of the lens within the visible range. The predetermined feature may in particular comprise an illumination-dependent transmission coefficient of the lens within the visible range, linked to photochromic properties of the lens. In this case, the electronic device 2 is programmed to determine the plurality of corrected images so that:

when the predetermined optical feature of the tested lens is representative of such photochromic properties, and when the measured value is representative of the presence of intense UV-light in the individual's environment 3, then, this sequence of corrected images evidences a progressive darkening of the scene virtually viewed through the lens.

The corresponding darkening speed may in particular depend on the measured value of the first parameter, such that this darkening speed increases based on the luminous intensity of the light 4 measured by means of the sensor.

In a variant, the device is programmed to determined a calculated value of a second parameter, linked to the luminous intensity of a light that would be received by the individual's eyes when said lens is placed in front of his eyes while the image is captured in step b), as a function of said measured value of said first parameter and of said predetermined optical feature of the lens, and said corrected image is determined by taking into account the calculated value of the second parameter.

This second parameter linked to the luminous intensity of the light that would be received by the individual's eyes when said lens is placed in front of his eyes while the images are captured in step b), is a luminous intensity, and/or a luminance, and/or an illumination, and said calculated value of the second parameter is determined as a function of said measured value of the corresponding luminous intensity, and/or luminance and/or illumination measured in step c).

In this variant, the features of the graphical representation of light are determined taking into account the calculated value of the second parameter.

The number and/or luminosity and/or shape and/or color of the elements of the graphical representation are then determined based on said calculated value of the second parameter. In particular, the number of elements representing the rays of light going through the lens toward the eyes of the individual is increasing with a higher calculated value of this second parameter.

According to another optional feature of the device and method of the invention, the electronic device 2 may be programmed to determine whether the light 4, whose luminous intensity is estimated via said measured value:

1) comes from a part of the environment 3 located in front of the camera 21, on the same side of the headset 23 than the camera field of view 210, or, on the contrary, 2) comes from another part of the environment 3, located at the opposite of the camera field of view 210.

In this case, the electronic device 2 may be programmed to determine the corrected image such that it furthermore depends on which side of the headset this light 4 is coming from.

More precisely, in case 1), that is to say when said light 4 is coming from the front of the headset 23, the corrected image is determined as explained above, thus representing said light potentially going through or being stopped by the tested lens.

In case 2), that is to say when said light 4 is coming from the back of the headset 23, the corrected image is determined to represent graphically said light 4, virtually incident on the lens from the back, on the eye-side face of the lens, partially transmitted by the lens, and partially reflected toward the individual's eye 11 by the lens.

In case 2), the graphical representation of said light 4 may comprise, as in case 1), elements representing light rays or photons, whose geometrical and/or display features depend on the measured value of the first parameter, and on the predetermined optical feature of the lens. In particular, this graphical representation may comprise elements representing optical rays and/or photons bouncing on the eye-side face of the lens, these elements being for instance all the more numerous as the reflection coefficient of eye-side face of the lens within the predetermined wavelength range is high.

According to yet another optional feature of the device and method, the electronic device 2 may be programmed to determine a position of a source of said light 4 having said wavelength comprised in said predetermined wavelength range. This source may correspond for instance to the light torch 41 represented on FIG. 1.

The position of the source may for example be determined in the two-dimensional captured image, by processing this image using a light-source search algorithm. A three-dimensional position of the source, in the physical environment 3 of the individual, may also be deduced from the image processing.

The electronic device 2 may also be programmed to determine the corrected image as a function of the position of the source of said light 4. For examples, the above-mentioned straight lines representing light rays may all intersect in a given point of the corrected image corresponding to the position of the source, as represented on FIGS. 4 and 5, to concisely represent that these light rays arise from said source.

As described above, the invention provides for a method for virtual testing of the above-mentioned lens using said electronic device 2.

In a preliminary step of this method, the headset 23 is placed on the individual's head 1, so that the headset screen 20 is disposed in front of the individual's eyes 11.

Optionally, in this preliminary step, a source emitting radiations in the predetermined wavelength range is placed in front of the individual, in the field of view 210 of the camera 21.

The headset is preferably manually held by the individual, in front of his/her eyes 11. This enables the individual to quickly place the headset 23 on his head 1 or remove it, while he/she is wearing or not spectacles.

While the steps of the method are performed, the individual may move freely with headset 23 on his head 1, to explore his/her environment 3.

In this method, according to a particularly remarkable feature, steps a), b) and c), that have been described above in detail, are performed.

As represented schematically on FIG. 2, steps a) and b) are here performed in parallel, and step c) is subsequently executed.

In other, non-represented embodiments of the method, steps a), b) and c) may me performed in this order, one after the other.

The ensemble of steps a), b), and c) may also be repeated several times, a different lens being virtually tested during each repetition of this ensemble of steps, so that the individual can compare theses lenses to each other, in terms of protective effect.

During this sequence of virtual tests, the predetermined optical feature associated to each of these tested lens may be received by the electronic device 2 from a distinct electronic apparatus, such as a tablet, remotely, preferably wirelessly connected to the electronic device.

The invention claimed is:

1. A method for virtual testing of at least one lens having a predetermined optical feature and configured to be used in eyeglasses by an individual, using a headset including at least a screen, an image capture apparatus, and a sensor, the headset being configured to be placed on a head of an individual such that said screen is disposed in front of at least one eye of the individual, the image capture apparatus being configured to capture an image of the environment of the individual, the sensor being configured to measure a value of a first parameter representative of a luminous intensity, and/or a luminance, and/or an illumination, within a predetermined wavelength range, of a light present in said environment of the individual with a wavelength comprised in the predetermined wavelength range the method comprising the following steps:

a) capturing at least an image of said environment of the individual with said image capture apparatus;

b) measuring said measured value of said first parameter corresponding to said image captured in step a); and c) displaying on said screen of the headset a corrected image based on said captured image, the corrected image comprising, when the measured value is above a given threshold, a graphical representation of the light superimposed onto the captured image, the graphical representation comprising elements representing light rays and/or photons, wherein the optical feature of the lens comprises at least one of: a reflection coefficient of an object-side face of the lens within the predetermined wavelength range, a transmission coefficient of the lens within the predetermined wavelength range, and a reflection coefficient of an eye-side face of the lens within the predetermined wavelength range, and the graphical representation of the light depends on the optical feature of the lens to evidence whether, within the predetermined wavelength range, the lens transmits and/or reflects and/or stops the light.

2. The method according to claim 1, wherein, in step c), the graphical representation having features that depend on said optical feature of the lens.

3. The method according to claim 2, wherein said graphical representation comprises features that depend on said measured value of the first parameter.

4. The method according to claim 2, wherein said features of the graphical representation comprise geometrical and/or display features.

5. The method according to claim 2, wherein, in step a), a plurality of images is captured, and in step c), a plurality of corrected images is determined.

6. The method according to claim 1, wherein said graphical representation comprises features that depend on said measured value of the first parameter.

7. The method according to claim 1, wherein, in step a), a plurality of images is captured, and in step c), a plurality of corrected images is determined.

8. The method according to claim 7, wherein, in step c), the plurality of corrected images comprises an animated graphical representation of said light having said wavelength comprised in said predetermined wavelength range, said animated graphical representation comprising elements representing light rays and/or photons, a frequency of appearance of said elements in said plurality of corrected images depending on said measured value of the first parameter and on said optical feature of the lens.

9. The method according to claim 1, wherein in step b), said measured value is determined by a direct measurement of said first parameter in said environment.

10. The method according to claim 1, wherein in step b), said measured value is determined by an indirect measurement of said first parameter on said image captured in step a).

11. The method according to claim 1, wherein in step b), said predetermined wavelength range comprises wavelengths in the visible blue range, between 400 and 460 nanometers and/or in the Ultra-Violet range, between 280 and 400 nanometers.

12. The method according to claim 1, further comprising determining a position of a source of said light having said wavelength comprised in said predetermined wavelength range, in said captured image, wherein, in step c), said position is taken into account to determine said corrected image.

13. An electronic device for virtual testing of at least one lens having a predetermined optical feature and configured to be used in eyeglasses by an individual, the electronic device comprising:

a headset comprising at least a screen, the headset configured to be placed on the head of an individual such that said screen is disposed in front of one eye of the individual, an image capture apparatus configured to capture an image of the environment of the individual, and a sensor configured to measure a value of a first parameter representative of a luminous intensity, and/or a luminance, and/or an illumination, within a predetermined wavelength range, of a light present in said environment of the individual with a wavelength comprised in the predetermined wavelength range, said device being programmed to execute the following steps:

a) capturing at least an image of said environment of the individual with said image capture apparatus, b) measuring said measured value of said first parameter corresponding to said image captured in step a), c) displaying on said screen of the headset a corrected image based on said captured image, the corrected image comprising, when the measured value is above a given threshold, a graphical representation of the light superimposed onto the captured image, the graphical representation comprising elements representing light rays and/or photons, wherein the optical feature of the lens comprises at least one of: a reflection coefficient of an object-side face of the lens within the predetermined wavelength range, a transmission coefficient of the lens within the predetermined wavelength range, and a reflection coefficient of an eye-side face of the lens within the predetermined wavelength range, and the graphical representation of the light depends on the optical feature of the lens to evidence whether, within the predetermined wavelength range, the lens transmits and/or reflects and/or stops the light.

* * * * *